(12) United States Patent
Warr et al.

(10) Patent No.: US 12,378,500 B2
(45) Date of Patent: Aug. 5, 2025

(54) LIQUID LAUNDRY PRODUCT COMPRISING A FRAGRANCE COMPOSITION COMPRISING ISOPULEGOL

(71) Applicant: TAKASAGO INTERNATIONAL CORPORATION, Tokyo (JP)

(72) Inventors: Jonathan Warr, Paris (FR); Johan Poncelet, Paris (FR)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 17/331,803

(22) Filed: May 27, 2021

(65) Prior Publication Data

US 2021/0301219 A1   Sep. 30, 2021

Related U.S. Application Data

(62) Division of application No. 16/078,228, filed as application No. PCT/JP2017/006961 on Feb. 23, 2017, now abandoned.

(30) Foreign Application Priority Data

Feb. 24, 2016   (EP) .................................. 16305216

(51) Int. Cl.
| | | |
|---|---|---|
| *C11B 9/00* | (2006.01) | |
| *A61K 8/34* | (2006.01) | |
| *A61L 9/03* | (2006.01) | |
| *A61L 9/04* | (2006.01) | |
| *A61L 9/12* | (2006.01) | |
| *A61L 9/14* | (2006.01) | |
| *C11D 3/50* | (2006.01) | |

(52) U.S. Cl.
CPC .............. *C11B 9/0034* (2013.01); *A61K 8/34* (2013.01); *A61L 9/03* (2013.01); *A61L 9/042* (2013.01); *A61L 9/044* (2013.01); *A61L 9/048* (2013.01); *A61L 9/12* (2013.01); *A61L 9/14* (2013.01); *C11D 3/50* (2013.01); *A61K 2800/10* (2013.01)

(58) Field of Classification Search
CPC ............ C11B 9/0034; A61K 8/34; C11D 3/50
See application file for complete search history.

(56) References Cited

U.S. PATENT DOCUMENTS

| | | | |
|---|---|---|---|
| 4,847,292 A | 7/1989 | Katz et al. | |
| 4,853,413 A | 8/1989 | Katz et al. | |
| 5,773,410 A * | 6/1998 | Yamamoto | C11B 9/0034 512/23 |
| 8,603,962 B2 * | 12/2013 | Bastigkeit | C11D 3/48 510/330 |
| 2005/0129721 A1 | 6/2005 | Ishida et al. | |
| 2008/0112910 A1 | 5/2008 | Ishida et al. | |
| 2011/0081393 A1 | 4/2011 | Komatsuki et al. | |
| 2012/0087828 A1 | 4/2012 | Uchiyama et al. | |
| 2013/0131169 A1 | 5/2013 | Komatsuki et al. | |

FOREIGN PATENT DOCUMENTS

| | | | |
|---|---|---|---|
| CN | 103655243 A | 3/2014 | |
| EP | 1496095 A1 | 1/2005 | |
| EP | 1875902 A1 | 1/2008 | |
| EP | 2716303 A1 | 4/2014 | |
| JP | 63-199293 A | 8/1988 | |
| JP | H08-40959 A | 2/1996 | |
| JP | 2011-79953 A | 4/2011 | |
| WO | WO-0205772 A1 * | 1/2002 | ............... C11D 3/50 |
| WO | WO-02090479 A1 * | 11/2002 | ............... A61L 9/01 |
| WO | WO-02090480 A1 * | 11/2002 | ............... A61L 9/01 |
| WO | 03/074622 A1 | 9/2003 | |
| WO | WO-2013156371 A1 * | 10/2013 | ............... C11D 1/62 |

OTHER PUBLICATIONS

Communication dated Mar. 16, 2021, from the Japanese Patent Office in Application No. 2018-532334.
Y. Okazaki et al. "The Odour of Glandular Secretion and Human Emotion-Animal Perfume Materials and Human Body Odour Related Chemicals—" Flavours, Fragrances and Essential Oils, vol. 3, Oct. 15-19, 1995 (pp. 385-391).
Torii et al. "Effects of Odors on Contingebt Negative Variation (CNV)" 19th Symposium of Taste and Smell, Sep. 11, 1985 (pp. 65-68).
Written Opinion (PCT/ISA/237) issued by the International Searching Authority in corresponding International Application No. PCT/JP2017/006961, on May 9, 2017.
International Search Report (PCT/ISA/210), issued by International Searching Authority in corresponding International Application No. PCT/JP2017/006961, on May 9, 2017.

* cited by examiner

*Primary Examiner* — Rayna Rodriguez
(74) *Attorney, Agent, or Firm* — Sughrue Mion, PLLC

(57) ABSTRACT

A method for imparting a stimulating effect to a non-ingestible consumer product includes adding a fragrance composition to the consumer product. The consumer product is selected from a household product, a laundry product, a personal care product and a cosmetic product. The fragrance composition contains from about 0.2 wt % to less than 10 wt % of isopulegol, based on the total weight of the fragrance composition.

8 Claims, 6 Drawing Sheets

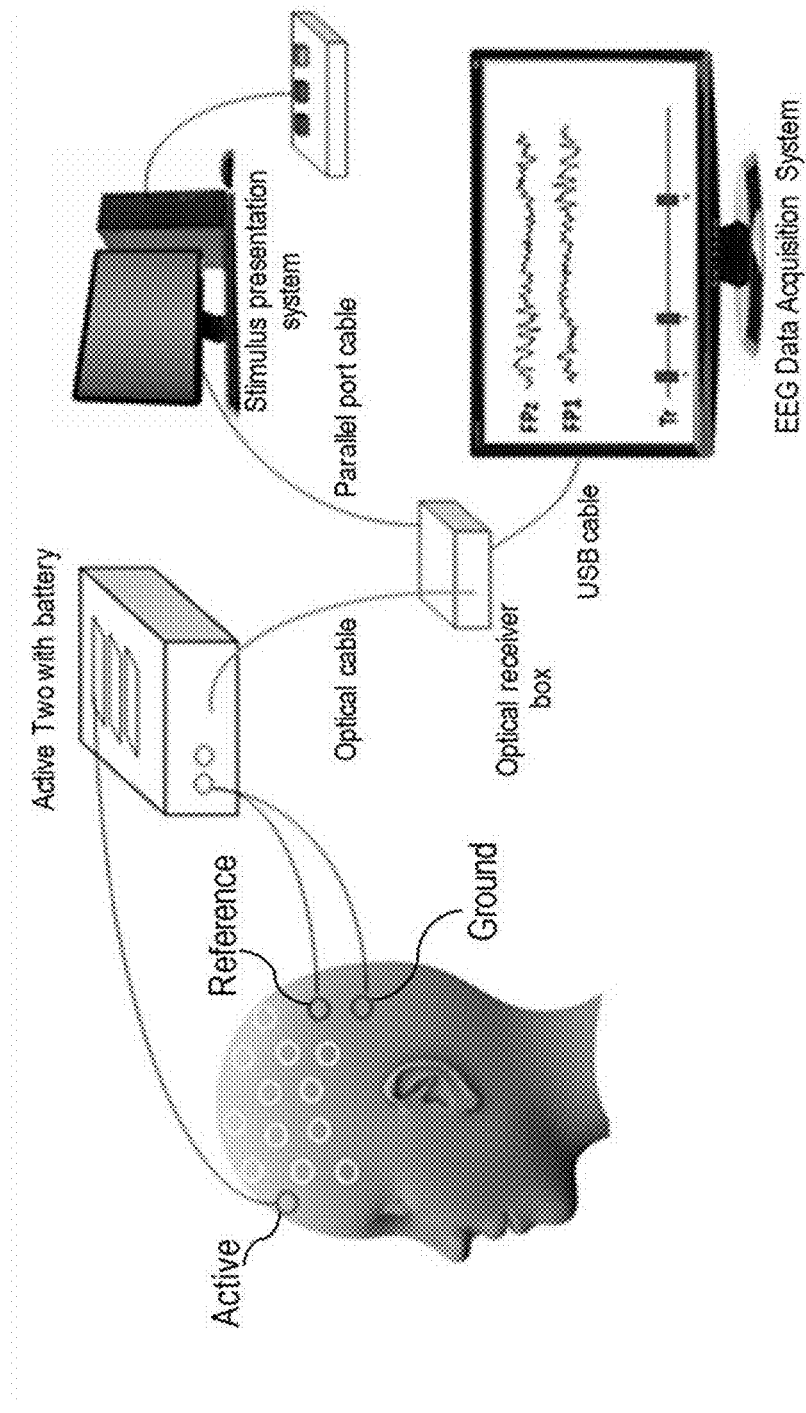

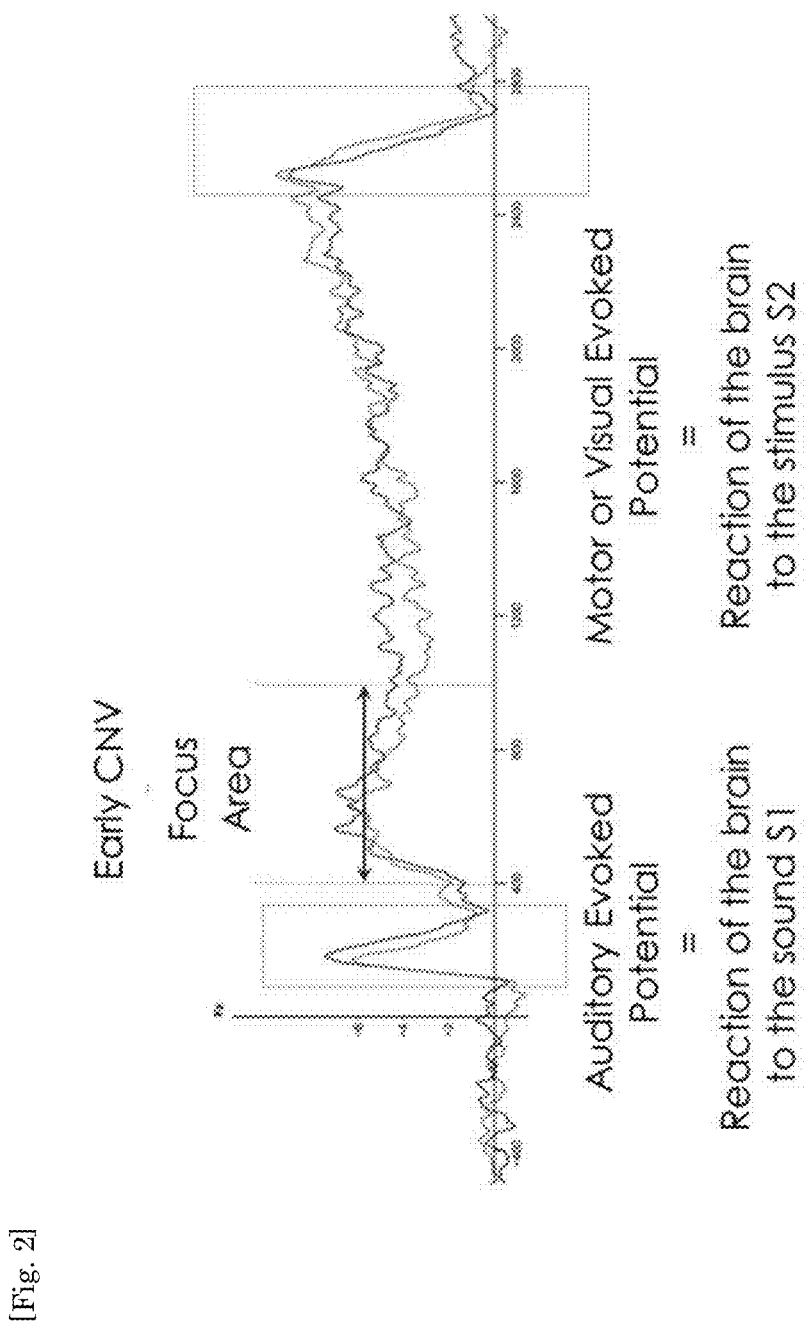
[Fig. 2]

[Fig. 3]
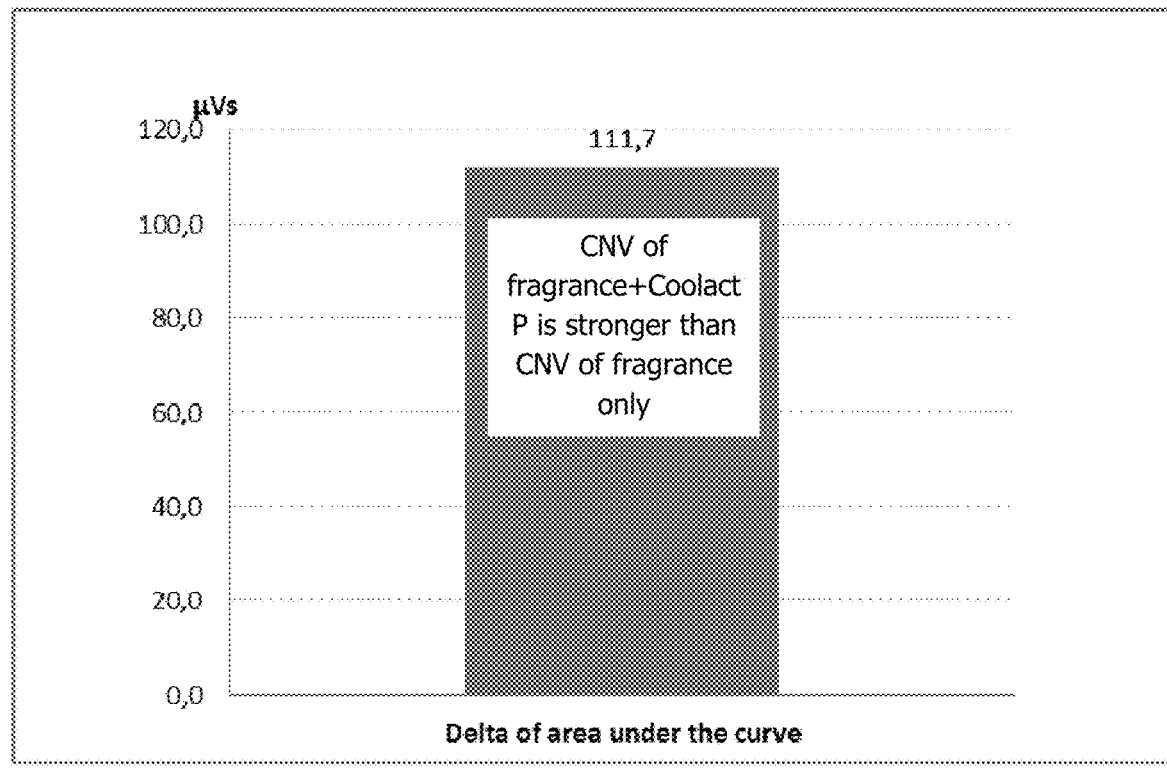
[Fig. 4]
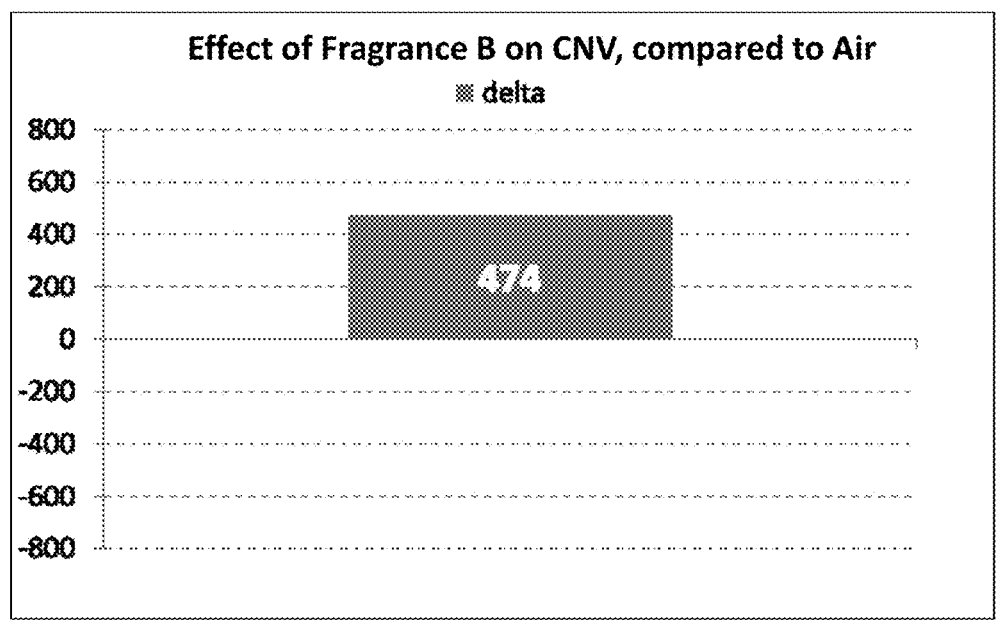

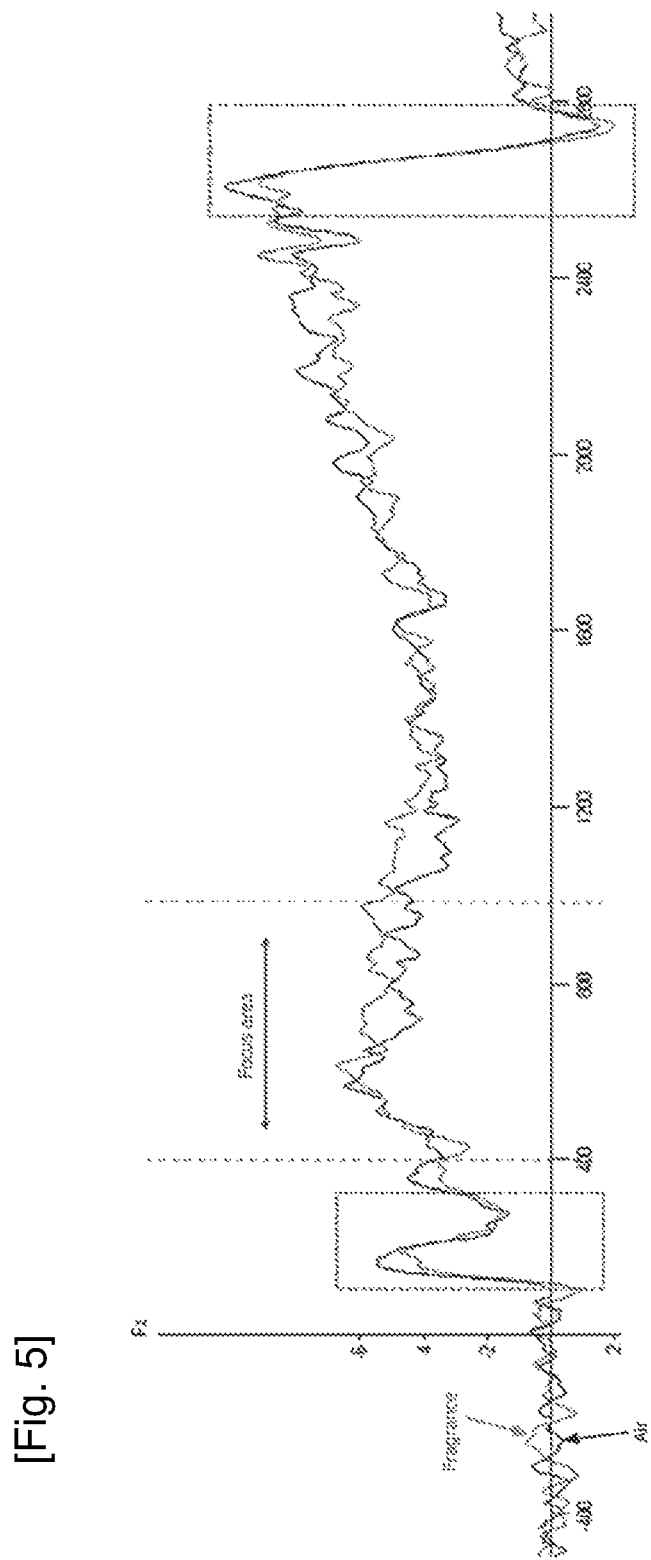
[Fig. 5]

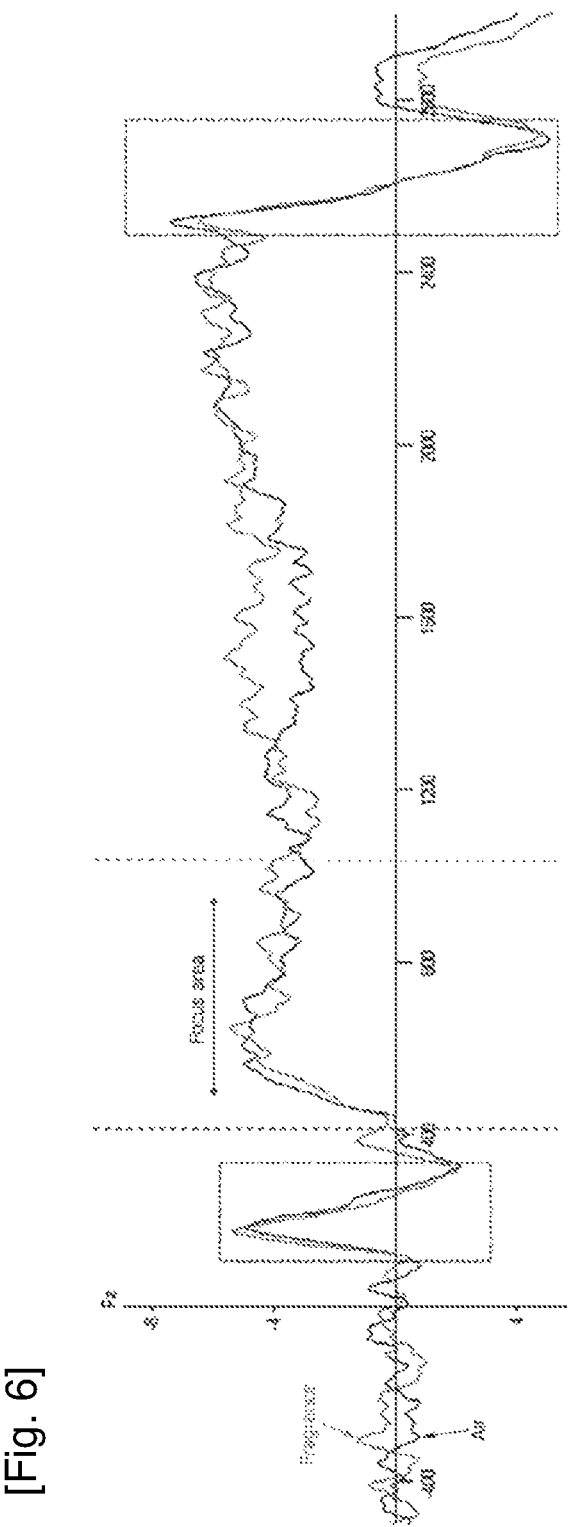
[Fig. 6]

[Fig. 7]
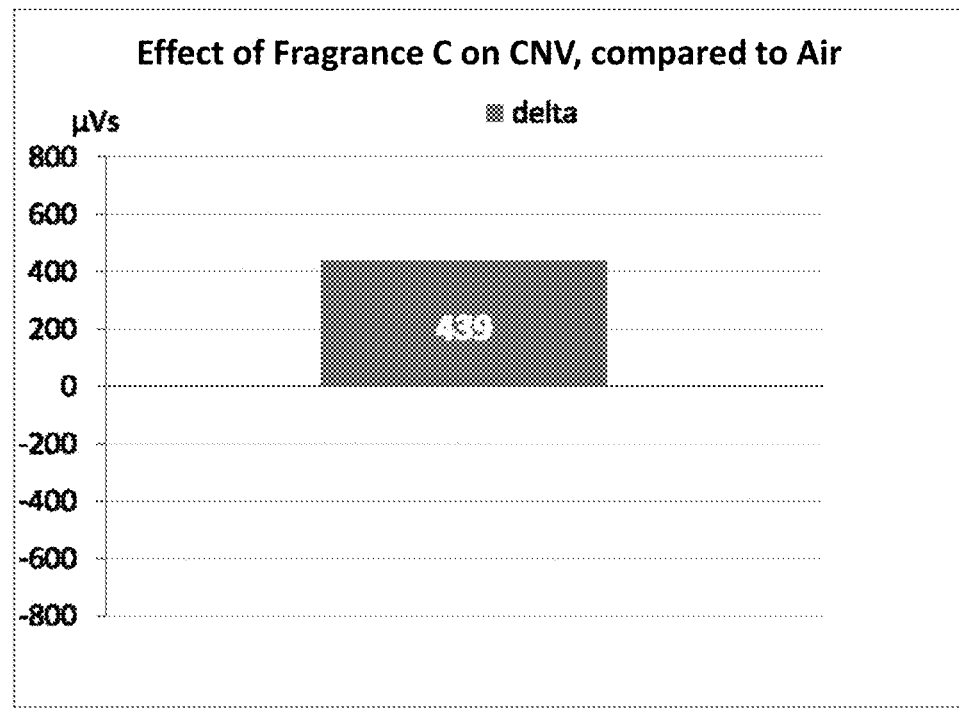

LIQUID LAUNDRY PRODUCT COMPRISING A FRAGRANCE COMPOSITION COMPRISING ISOPULEGOL

CROSS-REFERENCE TO THE RELATED APPLICATIONS

This application is a divisional of U.S. patent application Ser. No. 16/078,228, filed Aug. 21, 2018, which is a National Stage of International Application No. PCT/JP2017/006961, filed Feb. 23, 2017, which claims priority from European Patent Application No. 16305216.0, filed Feb. 24, 2016, the disclosures of all of which are incorporated herein in their entirety by reference.

TECHNICAL FIELD

The present invention relates to a stimulating agent comprising isopulegol. The invention also relates to a method for imparting a stimulating effect to a consumer product. The invention further relates to a method of giving a stimulative effect to a person by the evaporation and inhalation of a stimulating agent as defined above.

BACKGROUND ART

There is a growing demand from consumers for products which boost morale, provide a relaxing effect or help counter the effect of stress. EP-A-2 716 303 (PTL 1) describes a psychic energizer agent and composition, the effects of which are assessed by a method called Contingent Negative Variation (CNV). Fragrance materials which have a stimulant effect are also described e.g. in JP-A-63-199293 (PTL 2) and EP-A-1 875 902 (PTL 3), the former application also describes a CNV method of measuring a stimulating effect. CNV is a well-known method of indexing gradual potential changes in human brain, which was first described in 1964 in an article published in Nature. CNV relates to changes of mental processes and arousal levels such as attention, expectation, and anticipation. It is known that when the arousal level is high, an early component of CNV increases compared to normal state and when the arousal level is low, an early component of CNV decreases. For example, it was reported that when subjects smelled a jasmine oil, which is empirically known to have a stimulant effect, an early component of CNV increased whereas when subjects smelled a lavender type fragrance, which is empirically known to have a calming effect, an early component of CNV decreased (see for example Tori et al., 19th Symposium of Taste and Smell, Sep. 11, 1985 (NPL 1)). Stimulative and sedative effects of odorous compounds, as determined by CNV, is reported e.g. by Okazaki et al. (Flavours, Fragrances and Essential Oils. Proceedings of the 13th International Congress of Flavours, Fragrances and Essential Oils, Istanbul, Turkey, 15-19 Oct. 1995. Vol. 3) (NPL 2).

CITATION LIST

Patent Literature

[PTL 1] EP-A-2 716 303
[PTL 2] JP-A-63-199293
[PTL 3] EP-A-1 875 902

Non Patent Literature

[NPL 1] Tori et al., 19th Symposium of Taste and Smell, Sep. 11, 1985

[NPL 2] Okazaki et al., Flavours, Fragrances and Essential Oils., Proceedings of the 13th International Congress of Flavours, Fragrances and Essential Oils, Istanbul, Turkey, 15-19 Oct. 1995., Vol. 3

SUMMARY OF INVENTION

Technical Problem

An object of the present invention is to provide a method for imparting a stimulating effect to a consumer product.

Solution to Problem

In one aspect, the present invention relates to a method for imparting a stimulating effect to a non-ingestible consumer product, which comprises adding a fragrance composition to said consumer product, wherein the fragrance composition comprises from about 0.2 wt % to less than 10 wt % of isopulegol, based on the total weight of the fragrance composition.

In another aspect, the present invention relates to a method of giving a stimulative effect to a person by the evaporation and inhalation of a fragrance composition comprising from about 0.2 wt % to less than 10 wt % of isopulegol, based on the total weight of the fragrance composition.

In yet another aspect, the present invention relates to the (non-therapeutic) use of isopulegol, or of a fragrance composition comprising from about 0.2 wt % to less than 10 wt % of isopulegol, based on the total weight of the fragrance composition, as a stimulating agent.

Advantageous Effects of Invention

In the present invention, it is possible to impart a stimulating effect to a non-ingestible consumer product.

BRIEF DESCRIPTION OF DRAWINGS

FIG. 1 is a schematic representation of the CNV technique.

FIG. 2 represents a typical CNV recording, where potential changes in human brain are detected in the focus area.

FIG. 3 represents the difference between the area under the curve of (fragrance A+isopulegol) and the area under the curve of fragrance A alone, as calculated from CNV recording (not shown).

FIG. 4 represents the difference between the area under the curve of fragrance B and the area under the curve of air as calculated from CNV recording (shown in FIG. 5).

FIG. 5 is a CNV recording of Fragrance B (gray line) compared to air (black line).

FIG. 6 is a CNV recording of Fragrance C (gray line) compared to air (black line).

FIG. 7 represents the difference between the area under the curve of fragrance C and the area under the curve of air as calculated from CNV recording (shown in FIG. 6). The area under the curve is calculated for values between the dashed lines in FIGS. 5 and 6.

DESCRIPTION OF EMBODIMENTS

According to a first aspect, the present invention relates to a method for imparting a stimulating effect to a household, laundry, personal care, or cosmetic product, which comprises adding a fragrance composition to said product, wherein the fragrance composition comprises from about 0.2 wt % to less than 10 wt % of isopulegol, preferably (−) isopulegol, based on the total weight of the fragrance composition.

In the context of the present invention, the term "stimulating effect" refers to an effect uplifting the arousal level of a human subject, as determined by Contingent Negative Variation (CNV). In the context of the present invention, the terms "stimulating", "energizing", "invigorating", "arousing" and "awakening" may be interchangeably used. Likewise, the term "stimulating agent" is to be understood in the context of the present invention as an agent providing a stimulating effect. Isopulegol is available either as a racemic mixture (CAS 7786-67-6), or as the (−)-isomer (CAS 89-79-2). In one embodiment isopulegol is available as Coolact (registered trademark) P, a product from Takasago. The isopulegol of the invention may have an optical isomer and chemical purity of greater than 90%, preferably greater than 95%, more preferably greater than 97.5%, and even more preferably greater than 99%. Isopulegol purity is determined by gas chromatography using the method described in U.S. Pat. No. 5,773,410 by summing the area percent of impurity peaks and subtracting these from the total measured area which is taken to be 100%.

Whilst isopulegol is known as a cooling agent that provides a cooling effect to the skin when applied thereto, the inventors have now surprisingly found that isopulegol also produces a stimulating effect, notably when formulated into a fragrance composition that is distributed and then evaporates in the air.

In one embodiment, isopulegol is present in a fragrance composition. The fragrance composition advantageously comprises from about 0.2 to less than 10 wt %, about 0.2 to about 9 wt %, about 0.2 to about 8 wt %, about 0.2 to about 7 wt %, about 0.2 to about 6 wt %, about 0.2 to about 5 wt %, about 0.2 to about 4 wt % or about 0.2 to about 3 wt % of isopulegol, based on the total weight of the fragrance composition. The fragrance composition may comprise from about 1 to about 9 wt %, about 1 to about 8 wt %, about 1 to about 7 wt %, about 1 to about 6 wt %, about 1 to about 5 wt %, about 1 to about 4 wt % or about 1 to about 3 wt % of isopulegol, based on the total weight of the fragrance composition. The fragrance composition may also comprise from about 2 to about 9 wt %, about 2 to about 8 wt %, about 2 to about 7 wt %, about 2 to about 6 wt %, about 2 to about 5 wt %, or about 2 to about 4 wt % of isopulegol, based on the total weight of the fragrance composition.

In one embodiment, the fragrance composition does not comprise any of 1-menthoxy-propanediol, 1-menthol and p-menthane-3,8-diol. In another embodiment, the fragrance composition does not comprise a diester of the following formula.

[Chem. 1]

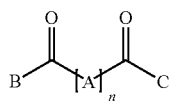

In the above formula, A represents $CH_2$ or CH=CH, n represents an integer of 0 to 4 when A is $CH_2$ or 1 when A is CH=CH, B is an alcohol residue having 10 to 18 carbon atoms and containing a para-menthane skeleton, which may be substituted, and C is an alcohol residue having 6 to 18 carbon atoms, which may be substituted.

In another embodiment the fragrance composition does not comprise a salicylic ester of the following formula.

[Chem. 2]

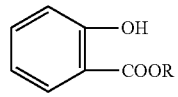

In the above formula, R represents a hydrocarbon group having 1 to 18 carbon atoms which may be substituted.

The fragrance composition typically comprises, in addition to isopulegol, a perfume ingredient, and preferably at least two, such as at least five, or at least eight distinct perfume ingredients. It can comprise highly complex mixtures of perfume ingredients, chosen to provide any desired odour. The perfume ingredient typically is an olfactively active material acting as a malodour counteractant, which do not necessarily provide a pleasant smell. Perfume ingredients typically used in the field of perfumery and suitable for the purposes of the present invention are described more fully in S. Arctander, Perfume Flavors and Chemicals 1969, Vols. I and II, Montclair, N. J. and in The Merck Index, 8$^{th}$ edition, Merck & Co., Inc. Rahway, N. J. The term perfume ingredient encompasses naturally occurring as well as synthetic perfume materials known for use in perfumes, as well as animal oils. A perfume ingredient can also be any natural oil or extract, or chemical compound used in a fragrance composition. Natural oils and extracts are described in The Essential Oils by E Guenther published in 1949 by Van Nostrand and may include extracts, pressings, collection of exudates, and distillates from any part of suitable plants: roots, rhizomes, bulbs, corms, stem, bark, heartwood, leaves, flowers, seeds and fruit. Examples of such extracts and distillates include citrus fruit oils such as orange, mandarin, grapefruit, lime or lemon oils, tree oils such as pine, or cedarwood, herb oils such as peppermint, thyme, lavender, basil, rosemary, clove or flower extracts such as rose, jasmine, muguet, or geranium oil.

It may be preferred that each perfume ingredient has a molecular weight greater than 100 g/mol, preferably greater than 120 g/mol and lower than 325 g/mol, preferably lower than 300 g/mol. It may further be preferred that each perfume ingredient has a boiling point in the range 80-400° C., such as in the range 100-350° C., when measured at 760 mm Hg.

Advantageously, the perfume ingredient is selected from the following list.

$C_8$-$C_{18}$ hydrocarbons, preferably delta-3-carene, alpha-pinene, beta-pinene, alpha-terpinene, gamma-terpinene, p-cymene, bisabolene, camphene, caryophyllene, cedrene, farnesene, limonene, longifolene, myrcene, ocimene, valencene, and (E,Z)-1,3,5-undecatriene.

$C_2$-$C_{18}$ aliphatic alcohols, preferably hexanol, octanol, 3-octanol, 2,6-dimethylheptanol, 2-methylheptanol, 2-methyloctanol, (E)-3-hexenol, (E) and (Z)-3-hexenol, 1-octen-3-ol, mixtures of 3,4,5,6,6-pentamethyl-3/4-hepten-2-ol and 3,5,6,6-tetramethyl-4-methylene-heptan-2-ol, (E,Z)-2,6-nonadienol, 3,7-dimethyl-7-methoxyoctan-2-ol, 9-decenol, 10-undecenol, and 4-methyl-3-decen-5-ol.

$C_2$-$C_{18}$ aliphatic aldehydes and their acetals, preferably hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl- 5-heptenal, 10-undecenal, (E)-4-decenal, 2-dodecenal, 2,6,10-trimethyl-5,9-undecadienal, heptanal diethyl acetal, 1,1-dimethoxy-2,2,5-trimethyl-4-hexene, and citronellyl oxyacetaldehyde.

$C_3$-$C_{18}$ aliphatic ketones and oximes thereof, preferably 2-heptanone, 2-octanone, 3-octanone, 2-nonanone, 5-methyl-3-heptanone, 5-methyl-3-heptanone oxime, and 2,4,4,7-tetramethyl-6-octen-3-one.

$C_2$-$C_{18}$ aliphatic sulphur-containing compounds, preferably 3-methylthiohexanol, 3-methylthiohexyl acetate, 3-mercaptohexanol, 3-mercaptohexyl acetate, 3-mercaptohexyl butyrate, 3-acetylthiohexyl acetate, and 1-menthene-8-thiol.

$C_2$-$C_{18}$ aliphatic nitrile-containing compounds, preferably 2-nonenenitrile, 2-tridecenenenitrile, 2,12-tridecenenenitrile, 3,7-dimethyl-2,6-octadienenitrile, and 3,7-dimethyl-6-octenenitrile.

$C_2$-$C_{18}$ aliphatic carboxylic acids and esters thereof, preferably (E)- and (Z)-3-hexenyl formate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexyl butyrate, (E)- and (Z)-3-hexenyl isobutyrate, hexyl crotonate, ethyl isovalerate, ethyl 2-methylpentanoate, ethyl hexanoate, allyl hexanoate, ethyl heptanoate, allyl heptanoate, ethyl octanoate, ethyl (E,Z)-2,4-decadienoate, methyl 2-octynoate, methyl 2-nonynoate, allyl-2-isoamyloxyacetate, and methyl-3,7-dimethyl-2,6-octadienoate.

$C_4$-$C_{18}$ acyclic terpene alcohols, preferably citronellol, geraniol, nerol, linalool, lavandulol, nerolidol, farnesol, tetrahydrolinalool, tetrahydrogeraniol, 2,6-dimethyl-7-octen-2-ol, 2,6-dimethyloctan-2-ol, 2-methyl-6-methylene-7-octen-2-ol, 2,6-dimethyl-5,7-octadien-2-ol, 2,6-dimethyl-3,5-octadien-2-ol, 3,7-dimethyl-4,6-octadien-3-ol, 3,7-dimethyl-1,5,7-octatrien-3-ol, and 2,6-dimethyl-2,5,7-octatrien-1-ol.

$C_4$-$C_{18}$ acyclic terpene aldehydes and ketones, preferably geranial, neral, citronellal, 7-hydroxy-3,7-dimethyloctanal, 7-methoxy-3,7-dimethyloctanal, 2,6,10-trimethyl-9-undecenal, geranylacetone, and the dimethyl and diethyl acetals of geranial, neral, and 7-hydroxy-3,7-dimethyloctanal.

$C_4$-$C_{18}$ cyclic terpene alcohols, preferably alpha-terpineol, terpineol-4, menthan-8-ol, menthan-1-ol, menthan-7-ol, borneol, isoborneol, linalool oxide, nopol, cedrol, ambrinol, vetiverol, and guaiol.

$C_4$-$C_{18}$ cyclic terpene aldehydes and ketones, preferably fenchone, alpha-ionone, beta-ionone, alpha-n-methylionone, beta-n-methylionone, alpha-isomethylionone, beta-isomethylionone, alpha-irone, alpha-damascone, beta-damascone, beta-damascenone, delta-damascone, gamma-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H)-one, nootkatone, dihydronootkatone, alpha-sinensal, beta-sinensal, and methyl cedryl ketone.

$C_4$-$C_{18}$ cyclic alcohols, preferably 4-tert-butylcyclohexanol, 3,3,5-trimethylcyclohexanol, 3-isocamphylcyclohexanol, 2,6,9-trimethyl-Z2,Z5,E9-cyclododecatrien-1-ol, and 2-isobutyl-4-methyltetrahydro-2H-pyran-4-ol.

$C_4$-$C_{18}$ cycloaliphatic alcohols, preferably alpha-3,3-trimethylcyclohexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, and 1-(2,2,6-trimethylcyclohexyl)hexan-3-ol.

$C_4$-$C_{18}$ cyclic and cycloaliphatic ethers, preferably cedryl methyl ether, cyclododecyl methyl ether, (ethoxymethoxy)cyclododecane, alpha-cedrene epoxide, 3a,6,6,9a-tetramethyl-dodecahydronaphtho[2,1-b]furan, 3a-ethyl-6,6,9a-trimethyldodecahydro-naphtho[2,1-b]furan, 1,5,9-trimethyl-13-oxabicyclo[10.1.0]trideca-4,8-diene, rose oxide, and 2-(2,4-dimethyl-3-cyclohexen-1-yl)-5-methyl-5-(1-methylpropyl)-1,3-dioxane.

$C_4$-$C_{18}$ cyclic ketones, preferably 4-tert-butylcyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert-pentylcyclohexanone, 5-cyclohexadecen-1-one, 6,7-dihydro-1,1,2,3,3-pentamethyl-4(5H)-indanone, 9-cycloheptadecen-1-one, cyclopentadecanone, and cyclohexadecanone.

$C_4$-$C_{18}$ cycloaliphatic aldehydes, preferably 2,4-dimethyl-3-cyclohexenecarbaldehyde, 2-methyl-4-(2,2,6-trimethyl-cyclohexen-1-yl)-2-butenal, 4-(4-hydroxy-4-methylpentyl)-3-cyclohexenecarbaldehyde, and 4-(4-methyl-3-penten-1-yl)-3-cyclohexenecarbaldehyde.

$C_4$-$C_{18}$ cycloaliphatic ketones, preferably 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphthalenyl methyl ketone, methyl-2,6,10-trimethyl-2,5,9-cyclododecatrienyl ketone, and tert-butyl(2,4-dimethyl-3-cyclohexen-1-yl) ketone.

Esters of cyclic alcohols in $C_4$-$C_{18}$, preferably 2-tert-butylcyclohexyl acetate, 4-tert-butyl-cyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl isobutyrate, and 4,7-methanooctahydro-5 or 6-indenyl acetate.

Esters of cycloaliphatic carboxylic acids in $C_4$-$C_{18}$, preferably allyl 3-cyclohexylpropionate, allyl cyclohexyloxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, and ethyl 2-methyl-1,3-dioxolane-2-acetate.

$C_4$-$C_{18}$ aromatic hydrocarbons, preferably styrene and diphenylmethane.

$C_4$-$C_{18}$ araliphatic alcohols, preferably benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, and 1-(4-isopropylphenyl) ethanol.

Esters of araliphatic alcohols in $C_4$-$C_{18}$ and aliphatic carboxylic acids in $C_4$-$C_{18}$, preferably benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, alpha-trichloromethylbenzyl acetate, alpha,alpha-dimethylphenylethyl acetate, alpha,alpha-dimethylphenylethyl butyrate, cinnamyl acetate, 2-phenoxyethyl isobutyrate, and 4-methoxybenzyl acetate.

$C_2$-$C_{18}$ araliphatic ethers, preferably 2-phenylethyl methyl ether, 2-phenylethyl isoamyl ether, 2-phenylethyl 1-ethoxyethyl ether, phenylacetaldehyde dimethyl acetal, phenylacetaldehyde diethyl acetal, hydratropaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, and 4,4a,5,9b-tetrahydro-2,4-dimethylindeno[1,2-d]-m-dioxin.

$C_4$-$C_{18}$ aromatic and araliphatic aldehydes, preferably benzaldehyde, phenylacetaldehyde, 3-phenylpropanal, hydratropaldehyde, 4-methylbenzaldehyde, 4-methylphenylacetaldehyde, 3-(4-ethylphenyl)-2,2-dimethylpropanal, 2-methyl-3-(4-isopropylphenyl)propanal, 2-methyl-3-(4-tert-butylphenyl)propanal, 3-(4-tert-butylphenyl)propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylenedioxybenzaldehyde, 3,4-dimethoxybenzaldehyde, 2-methyl-3-(4-methoxyphenyl)propanal, and 2-methyl-3-(4-methylenedioxyphenyl)propanal.

$C_4$-$C_{18}$ aromatic and araliphatic ketones, preferably acetophenone, 4-methylacetophenone, 4-methoxyacetophenone, 4-tert-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert-butyl-1,1-dimethyl-4-indanyl methyl ketone, 1-[2,3-dihydro-1,1,2,6-tetramethyl-3-(1-methylethyl)-1H-5-indenyl]ethanone, and 5',6',7',8'-tetrahydro-3',5',5',6',8',8'-hexamethyl-2-acetonaphthone.

$C_4$-$C_{18}$ aromatic and araliphatic carboxylic acids and esters thereof, preferably phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, and ethyl 3-methyl-3-phenylglycidate.

Nitrogen-containing aromatic compounds in $C_4$-$C_{18}$, preferably 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenenitrile, 5-phenyl-3-methylpentanenitrile, methyl anthranilate, methyl N-methylanthranilate, Schiff bases of methyl anthranilate with 7-hydroxy-3,7-dimethyloctanal, 2-methyl-3-(4-tert-butylphenyl)propanal, 2,4-dimethyl-3-cyclohexene-carbaldehyde, 6-isopropylquinoline, 6-isobutylquinoline, 6-sec-butylquinoline, indole, skatole, 2-methoxy-3-isopropylpyrazine, and 2-isobutyl-3-methoxypyrazine.

Phenols, phenyl ethers and phenyl esters, preferably estragole, anethole, eugenol, eugenyl methyl ether, isoeugenol, isoeugenyl methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, and p-cresyl phenylacetate.

Heterocyclic compounds in $C_4$-$C_{12}$, preferably 2,5-dimethyl-4-hydroxy-2H-furan-3-one, 2-ethyl-4-hydroxy-5-methyl-22H-furan-3-one, 3-hydroxy-2-methyl-4H-pyran-4-one, and 2-ethyl-3-hydroxy-4H-pyran-4-one.

Lactones in $C_4$-$C_{18}$, preferably 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis and trans-li-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene 1,12-dodecanedioate, ethylene 1,13-tridecanedioate, coumarin, 2,3-dihydrocoumarin, and octahydrocoumarin.

The perfume ingredient present in the fragrance composition preferably does not contain ionizing functional groups, such as sulfonates, sulphates, phosphates or quaternary ammonium ions.

The fragrance composition of the invention may include one or more support materials, such as solvents or UV stabilizers. Examples of suitable solvents include hydrocarbons such as those sold under the trade name Isopar (registered trademark); ethers such as those sold under the Dowanol (registered trademark) trade name; benzyl benzoate; isopropyl myristate; dialkyl adipates; dialkyl succinates; dialkyl glutarates such as the dimethyl esters sold under the trade name Flexisolv (registered trademark); citrate esters, such as triethyl citrate and acetyl tributyl citrate; soybean methyl ester such as ME-S1885 (sold by Peter Cremer NA); diethyl phthalate; diethylene glycol monoethyl ether; 3-methoxy-3-methyl-1-butanol; dipropylene glycol; and isopropylidene glycerol sold under the Augeo (registered trademark) Clean Multi brand name. Examples of UV stabilisers include butyl methoxy dibenzoyl methane; bis ethylhexyloxyphenolmethoxyphenyl triazine; those sold under the Uvinol (registered trademark) trade name such as Uvinul D50 [bis(2,4-dihydroxyphenyl)-methanone], Uvinul MC80 (ethylhexyl methoxycinnamate) and Uvinul M40 (benzophenone-3); those sold under the Parsol (registered trademark) trade name, such as Parsol (registered trademark) MCX (same product as Uvinul MC80) and Parsol (registered trademark) 1789 (butyl methoxydibenzoylmethane); and those sold under the Tinogard (registered trademark) trade name, such as Tinogard (registered trademark) TT (pentaerythrityl tetra di-t-butyl hydroxyhydrocinnamate). When the fragrance composition is contained in a household product, the amount of solvent(s) may represent up to 60% by weight, such as up to 50% by weight, such as up to 40% by weight, of the total weight of the household product.

The fragrances compositions of the present invention impart a stimulating effect to non-ingestible consumer products into which they are incorporated.

In the context of the present invention, a non ingestible consumer product means a product or device for domestic use generally in the form in which it is sold but which excludes products which may be ingested either those which are deliberately ingested such as foodstuffs, snacks and pharmaceutical products and also those which may be accidentally ingested because they are used in the mouth such as toothpastes and mouthwashes. Such non ingestible consumer products include but are not limited to products for and/or methods relating to cleaning or treating hair, including bleaching, colouring, conditioning, shampooing, and styling products: products for cleaning or treating skin including bar soaps, liquid soaps, wet wipes, shower gels, bath foams, body washes, make up removers and exfoliating products, topically applied skin treatment products such as deodorants and antiperspirants, moisturizing creams, lotions, colour cosmetics, depilatory products, talcum powders, body sprays, eau de toilette and other fine fragrances; shaving products such as shaving gels, shaving foams and after shave balms, products for and/or methods relating to cleaning garments, soft furnishings, dishwashing, hard surfaces and any oiler surfaces in the home and domestic environment such as motor vehicle interiors including: air care including air fresheners and scent delivery systems, car care products, hand and machine dishwashing products, fabric conditioning products including fabric softeners and/or fragrancing products, laundry detergent products and tumble drier additives: hard surface cleaning and/or treatment products including dilutable and direct application products for kitchen and bathroom surfaces, glass and polished surfaces, floor cleaners and toilet bowl cleaners such as rim blocks, and other cleaning products for domestic use.

In one embodiment, the non-ingestible consumer product is selected from household products, laundry products, personal care products and cosmetic products.

Non-limiting examples of household products include air freshener dispenser devices, floor cleaners, kitchen or bathroom surface cleaners, and solid or liquid toilet rim blocks.

The air freshener dispenser device can be:
- a passive evaporative device selected from sprayers (such as automatic sprays, hand operated pressurised aerosol sprays or pump action sprays, as illustrated in US 2007/0122373), diffusers, gels, candles, waxes, wax melts, pot-pourri, impregnated papers and laminated cardboard, or
- an electrically powered air freshener dispenser device, preferably comprising a heating element, said electrically powered air freshener dispenser device being preferably a piezo-electric device or a plug, for example as described in U.S. Pat. No. 6,123,935.

In another embodiment, the household product of the invention is a kitchen or bathroom surface cleaner or a floor cleaner. Floor cleaners, also known as general purpose cleaner, also include carpet cleaner. They may be in several forms: isotropic liquids, thickened liquids with or without abrasive, pastes, gels, foams or sprays. They can be used directly from the bottle or after dilution in water. Various delivery methods have been devised for the convenience of the users, some are sprayed onto surfaces from trigger spray bottles, or alternatively they can be poured directly onto surfaces. They may contain additional ingredients such as acids for limescale removal, biocides for hygiene, or bleaching agents. A standard floor cleaner composition is given in Table 1 below, which summarises the main ingredients and their quantities (taken from Surfactant Science Series Vol. 67 Liquid Detergents chapter on Speciality Liquid Household Surface Cleaners p. 479, Table 4).

TABLE 1

| Ingredient | Example | Amount wt % |
|---|---|---|
| Anionic surfactant | Alkylbenzene sulphonate, as supplied by Shell as Dobs 055, alkane sulphonate eg Hostaspur SAS60 | 0-35 |
| Nonionic surfactant | Ethoxylated alcohol eg Neodol 9-11 6EO, mixed ethoxy/propoxy alcohol such as the pluronic series from BASF, amine oxide, alkanolamides and betaines | 1-35 |
| Hydrotropes | Sodium cumene sulphonate or xylene sulphonate | 0-10 |
| Builder/sequestrant | Citrates, EDTA salts, phosphonate salts, lactic acid and polyacrylates | 0-10 |
| Solvent | Lower alcohols, glycol ethers, benzyl alcohol, or hydrocarbons eg limonene | 0.5-50 |
| Disinfectant | Hypochlorite bleach, pine oil, lower alcohols, quaternary ammonium salts | 0-15 |
| Perfume, colour, thickening polymer, sequestrant, preservatives | | 0.1-3 |
| Water | | To 100 |

Solid toilet rim blocks are intended to be located under the rim of a lavatory bowl or urinal such that, during a flushing cycle, water from the cistern flows over the block thereby dissolving a portion of the toilet rim block. The invention also relates to cageless rim blocks which adhere directly to the surface of the lavatory pan, and to solid toilet cistern blocks which are placed in the cistern and dissolve slowly in the water contained therein. It will be appreciated that the solubility characteristics of these two products are quite different, since one is constantly under water while the other has intermittent short term contact with water. However, they both contain a surfactant, fillers, and a fragrance composition as defined according to the invention, and optionally bleaching agents, germicides and anti-limescale agents. Typical formulations are described in EP 0 462 643, GB 2 178 442, U.S. Pat. Nos. 4,874,536 and 8,658,588, which are incorporated herein by reference.

The liquid toilet rim blocks are devices that dispense liquid compositions directly into a lavatory bowl from under the rim of said bowl. Such liquid toilet rim blocks are usually attached by various means, such as hooks and the like, to the rim of the lavatory bowl. Every time a toilet equipped with a liquid toilet rim block is flushed, an amount of composition is dispensed into the lavatory bowl. Examples of liquid toilet rim blocks are given in WO 02/40792, EP 0 775 741, WO 01/94520 and US 2008/086801, which are incorporated herein by reference.

Personal care products may include products that can be applied to the skin, hair and nails either as leave on or rinse off product. Non-limiting examples of personal care products include shaving aids, shampoos, hair-conditioner products, leave-on-skin-care products, skin cleansing or washing products (such as a rinse-off skin cleansing or washing product), moist tissues, body sprays, deodorants or antiperspirants, eau de toilette and other fine fragrances. In one embodiment, the personal care product is an eau de toilette or a fine fragrance.

Shaving aids specifically include foams, gels, creams and bars (reference can be made for example to U.S. Pat. Nos. 7,069,658, 6,944,952, 6,594,904, 6,182,365, 6,185,822, 6,298,558 and 5,113,585).

Shampoos and hair conditioners specifically include two-in-one shampoos and shampoos especially formulated for dry or greasy hair or containing additives such as antidandruff agents. Hair conditioners may be rinse off or leave on hair conditioners also included are hair tonics, bleaches colorants, setting and styling products. Reference can be made for example to U.S. Pat. Nos. 6,162,423, 5,968,286, 5,935,561, 5,932,203, 5,837,661, 5,776,443, 5,756,436, 5,661,118, 5,618,523.

Leave-on-skin-care products comprise skin washing products, moist tissues, body sprays, deodorants and antiperspirants.

Skin washing products specifically include beauty and hygiene bar soaps, shower gels, liquid soaps, body washes, exfoliating gels and pastes (reference can be made for example to U.S. Pat. Nos. 3,697,644; 4,065,398; 4,387,040).

Moist tissues (wipes) specifically include skin cleansing wipes, baby wipes, make-up removal wipes and skin refreshing wipes (reference can be made for example to U.S. Pat. No. 4,775,582; WO02/07701; WO2007/069214 and WO95/16474).

Body sprays, deodorants and antiperspirants specifically include sticks, liquid roll-on applicators and pressurized sprays.

Eau de toilette formulations typically comprise (% by weight) from about 75% to about 80% ethanol, about 10% fragrance, less than about 1% UV filter, optionally less than about 1% colourants, optionally less than about 1% metal sequestrant, the balance to 100% being water.

Non-limiting examples of laundry products include powdered and liquid laundry detergents, detergent tablets and bars, and fabric softeners. In one embodiment, the laundry product is a fabric softener, a fabric conditioner or a laundry detergent. Fabric softeners and conditioners specifically include both conventional diluted (e.g. 2% to 8% by weight) liquid active concentration softeners and concentrated (e.g. 10% to 40% by weight) liquid active concentration softeners as well as fabric conditioners which may contain ingredients to protect colors or garment shape and appearance (reference can be made for 30 example to U.S. Pat. Nos. 6,335,315, 5,674,832, 5,759,990, 5,877,145, 5,574,179).

Laundry detergents, particularly liquid laundry detergents, specifically include light duty liquid detergents and heavy duty liquid detergents which may be structured multiphase liquids or isotropic liquids and which may be aqueous or non-aqueous liquids. These liquids may be in bottles or unit dose sachets and they may optionally contain bleaching agents or enzymes (reference can be made for example to U.S. Pat. Nos. 5,929,022, 5,916,862, 5,731,278, 5,470,507, 5,466,802, 5,460,752, and 5,458,810).

In another aspect, the present invention relates to a method of giving a stimulating effect to a person by the evaporation and inhalation of a fragrance composition comprising from about 0.2 wt % to less than 10 wt % of isopulegol, preferably (−) isopulegol, based on the total weight of the fragrance composition.

In yet another aspect, the present invention relates to the (non-therapeutic) use of isopulegol, or of a fragrance composition comprising from about 0.2 wt % to less than 10 wt % of isopulegol, based on the total weight of the fragrance composition, as a stimulating agent. The isopulegol is preferably (−) isopulegol.

The stimulating effect of isopulegol was determined by the CNV (Contingent Negative Variation) method as described below and briefly summarized in FIGS. 1 and 2.

The CNV was measured using a digital electroencephalograph BIOSEMi (registered trademark). Electrodes for the CNV measurement were placed at Fp1, Fp2, F4, Fz, F3, T7, C3, Cz, C4, T8, P4, Pz, P3, O1, Oz, O2 according to the international 10-20 system, electrodes for ear lobes were set to indifferent electrodes, and brain waves were recorded at a time constant of 5.0 seconds referenced to the linked earlobes. In order to check artifacts of eye movement to a brain wave, vertical and horizontal movements of the left eye were also recorded.

Confirmation of a stimulative effect of a sample was conducted by steps of delivering a warning stimulus S1 (tone of 60-65 dB), followed 2300 ms later by a second stimulus S2 (light source). Test fragrance compositions were inhaled from jars disposed a few (e.g. 15-20) centimetres from the subjects' nose during each period of acquisition. The averaged evoked potential was obtained by adding 20 times or more trials after removing any artifact such as eye movement using the Matlab (registered trademark) software with the open source Toolbox EEGlab and ERPlab. The base line was determined from an average voltage of a brain wave in a time period of 500 ms before S1. The evaluation of the CNV waveform was conducted according to the method of Tori et al. (op. cit.), in which CNV was evaluated by the area (unit: ms×mH) of an early component between 400 ms to 1,000 ms after the warning sound stimulus (S1).

The invention will be better understood in the light of the following examples given by way of illustration only.

Example 1

A fragrance composition having the following composition shown in Table 2 was prepared.

TABLE 2

| Fragrance A | |
|---|---|
| Ingredient | Wt % |
| Bergamot oil bergaptene free | 10.74 |
| Ethyl linalool | 5.37 |
| Exaltolide | 2.90 |
| Cis 3-hexenyl salicylate | 3.22 |
| Ionone beta | 2.69 |
| Iso super E | 10.74 |
| Linalyl acetate | 5.37 |
| Sandalore | 3.22 |
| Hedione | 42.86 |
| Orange oil Pera Brazil | 3.22 |
| Lemon oil Italian | 5.37 |
| Florol | 4.30 |

The effect of fragrance A, to which 2 wt % isopulegol was added, was determined by the CNV method as described above, using a panel of 7 subjects. Fragrance A was used as a control. It can be seen from FIG. 3 that isopulegol enhances the CNV activity of fragrance A; this enhancement is characteristic of a stimulating effect imparted by the inclusion of isopulegol.

Example 2

A fragrance composition having the following composition shown in Table 3 was prepared.

TABLE 3

| Fragrance B | |
|---|---|
| Ingredient | Wt % |
| Bergamot oil bergaptene free | 10.79 |
| Cedarwood oil Virginia | 3.78 |
| Cedramber | 7.56 |
| Ethyl linalool | 7.56 |

TABLE 3-continued

| Fragrance B | |
|---|---|
| Ingredient | Wt % |
| Hedione | 17.81 |
| Heliobouquet | 2.70 |
| Iso super E | 16.19 |
| Lemon oil Italian | 8.63 |
| Linalyl acetate | 8.63 |
| Orange oil Pera Brazil | 8.63 |
| Rosemary oil Morocco | 0.54 |
| Sandalore | 2.16 |
| Musk T | 3.02 |
| Isopulegol | 2.00 |

The effect of fragrance B was determined by the CNV method as described above, using a panel of 17 subjects. Air was used as a control. It can be seen from FIG. 4 that the CNV activity of fragrance B is significantly greater than that of air (mean ratio of +21%; t-test p<0.05). This effect is characteristic of a stimulating effect imparted by the inclusion of isopulegol.

Example 3

A fragrance composition having the following composition shown in Table 4 was prepared.

TABLE 4

| Fragrance C | |
|---|---|
| Ingredient | Wt % |
| Cedramber | 1.88 |
| Isopulegol | 3.00 |
| Ethyl linalool | 11.00 |
| Hedione | 12.00 |
| Heliobouquet | 1.56 |
| Cis 3-hexenyl salicylate | 3.13 |
| Orbitone BHT/Iso super E | 9.39 |
| Lemon oil Italian | 15.50 |
| Linalyl acetate | 9.50 |
| Mandarin oil Italian | 3.13 |
| Musk T | 3.13 |
| Rosemary oil Morocco | 0.63 |
| Sandalore | 1.25 |
| Dipropylene glycol | 14.25 |
| Exaltolide | 3.15 |
| Orange oil Pera White Brazil | 7.50 |

The effect of fragrance C was determined by the CNV method as described above, using a panel of 8 subjects. It can be seen from FIG. 7 that the CNV activity of fragrance C is significantly greater than that of air (mean ratio+31.9%). This effect is characteristic of a stimulating effect imparted by the inclusion of isopulegol.

Example 4

The following Eau de Toilette formulation can be used in the context of the invention (amounts are in percent by weight).

Ethanol 96: 77.51%
Fragrance C: 10.00%
Parsol 1789*: 0.20%
EDTA 2Na**: 0.001%
Demineralized water: qsp 100%

\* Parsol (registered trademark) 1789 is a UV absorber

\*\* EDTA is used as a sequestrant

While the invention has been described in detail and with reference to specific embodiments thereof, it will be apparent to one skilled in the art that various changes and modifications can be made therein without departing from the spirit and scope thereof. This application is based on European Patent Application No. 16 305 216.0 filed on Feb. 24, 2016, the entire subject matter of which is incorporated herein by reference.

INDUSTRIAL APPLICABILITY

In the present invention, it is possible to impart a stimulating effect to a non-ingestible consumer product.

The invention claimed is:

1. A liquid laundry product comprising a fragrance composition, wherein the fragrance composition comprises from about 0.2 wt % to about 2 wt % of isopulegol, based on the total weight of the fragrance composition, and wherein the fragrance composition comprises at least two perfume ingredients in addition to isopulegol, wherein said at least two perfume ingredients include linalyl acetate and musk T.

2. The liquid laundry product of claim 1, wherein isopulegol is (−) isopulegol.

3. The liquid laundry product of claim 1, which is selected from the group consisting of a liquid laundry detergent, a fabric softener and a fabric conditioner.

4. The liquid laundry product of claim 3, which is a liquid laundry detergent.

5. The liquid laundry product of claim 3, which is a fabric softener.

6. The liquid laundry product of claim 3, which is a fabric conditioner.

7. The liquid laundry product of claim 1, wherein the fragrance composition further comprises at least one ingredient selected from the group consisting of limonene, orbitone/iso E super, hedione, benzyl acetate, 4,7-methano-3a,4,5,6,7,7a-hexahydro-5 or 6-indenyl acetate, citronellol, linalool, terpineol, 2,6-dimethyl-7-octen-2-ol, decanal, pinene beta, 1,4-undecanolide, damascone delta, menthol, hexylcinnamaldehyde, geranial, phenyl ethyl alcohol, 4-hydroxy-3-ethoxybenzaldehyde, methyl ionone, 1,4-decanolide, dodecanal, 2-isobutyl-4-methyltetrahydro-2H-pyran-4-ol, geraniol, eugenol, beta-naphthyl methyl ether, ethyl 2-methyl-1,3-dioxolane-2-acetate, ethyl linalool, habanolide, 4,7-methano-3a,4,5,6,7,7a-hexahydro-5 or 6-indenyl propionate and 2-methyl-3-(4-isopropylphenyl)propanal.

8. The liquid laundry product of claim 3, which is a liquid laundry detergent in a unit dose sachet.

\* \* \* \* \*